United States Patent [19]

Goodman et al.

[11] Patent Number: 4,830,014
[45] Date of Patent: May 16, 1989

[54] SENSOR HAVING CUTANEOUS CONFORMANCE

[75] Inventors: David E. Goodman, San Francisco; James E. Corenman, Menlo Park; William New, Jr., Woodside; Mark Yelderman, Menlo Park, all of Calif.

[73] Assignee: Nellcor Incorporated, Hayward, Calif.

[21] Appl. No.: 70,619

[22] Filed: Jul. 7, 1987

Related U.S. Application Data

[63] Continuation of Ser. No. 873,129, Jun. 11, 1986, abandoned, which is a continuation of Ser. No. 539,865, Oct. 7, 1983, abandoned, which is a continuation-in-part of Ser. No. 493,442, May 11, 1983, abandoned.

[51] Int. Cl.$^4$ ............................................. A61B 5/02
[52] U.S. Cl. ..................................... 128/665; 128/666
[58] Field of Search ............... 128/633, 637, 640, 644, 128/665, 667, 664, 689, 690, 691

[56] References Cited

U.S. PATENT DOCUMENTS

| | | | |
|---|---|---|---|
| 3,167,658 | 1/1965 | Richter | 128/666 X |
| 3,599,629 | 8/1971 | Gordy | 128/640 |
| 3,602,213 | 8/1971 | Howell et al. | 128/2.05 F |
| 3,769,974 | 11/1973 | Smart et al. | 128/666 |
| 3,807,388 | 4/1974 | Orn et al. | 128/690 |
| 4,013,067 | 3/1977 | Kresse et al. | 128/660 |
| 4,091,803 | 5/1978 | Pinda | 128/666 |
| 4,305,401 | 12/1981 | Reissmueller et al. | 128/690 |
| 4,350,165 | 9/1982 | Striese | 128/640 |
| 4,370,984 | 2/1983 | Cartmell | 128/640 |
| 4,380,240 | 4/1983 | Jöbsis et al. | 128/633 |
| 4,406,289 | 9/1983 | Wesseling et al. | 128/690 |

FOREIGN PATENT DOCUMENTS

| | | | |
|---|---|---|---|
| 671279 | 10/1963 | Canada | 128/690 |
| 0019478 | 11/1980 | European Pat. Off. | |
| 2262952 | 10/1975 | France | |

OTHER PUBLICATIONS

Cohen, Arnon, "Photoelectric Determination of the Relative Oxygenation of Blood", Carnegie-Mellon University, Ph.D. Thesis, 1969, (pp. 57-77).

*Primary Examiner*—Edward M. Coven
*Attorney, Agent, or Firm*—Thomas L. Giannetti; Jeffrey H. Ingerman

[57] ABSTRACT

A sensor for trans-illumination of a blood perfused portion of flesh to measure light extinction during trans-illumination is disclosed. The sensor is preferably mounted on a fingertip but any digit or blood perfused portion of flesh will work. The sensor includes a first end for disposition on one side of the trans-illuminated flesh and a second end for disposition on the opposite and opposed side of the trans-illuminated flesh. A light source is mounted to the first side and a photo-sensor is mounted to the second side. If an elongated flexible strip is used, it is provided with adhesive and is suitably windowed that light is allowed to take an optical path through the finger. If no flexible strip is used, the two ends are aligned and secured to the flesh such that the light emitted takes an optical path through the finger. When the adhesive fastener is used, the effect of the light source and photo-detector substrates being integrated into the adhesive fastener is that they become, in effect, a part of the skin. The resulting device is resistant to accidental removal and avoids constriction of blood vessels. Most importantly, the low mass of the sensor itself and its conformance to, so as to effectively become a part of, the skin, prevents relative motion between the light source and sensor and the perfused flesh. This eliminates the common interference associated with the operation of conventional plethysmographs and oximeters.

2 Claims, 4 Drawing Sheets

U.S. Patent  May 16, 1989  Sheet 1 of 4  4,830,014
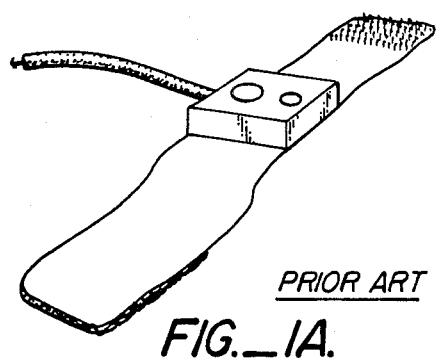
FIG._1A. PRIOR ART
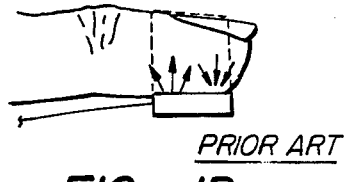
FIG._1B. PRIOR ART
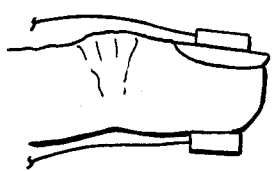
FIG._1C. PRIOR ART
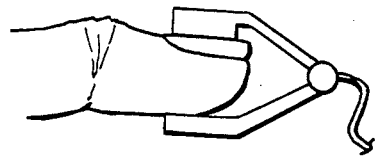
FIG._1D. PRIOR ART
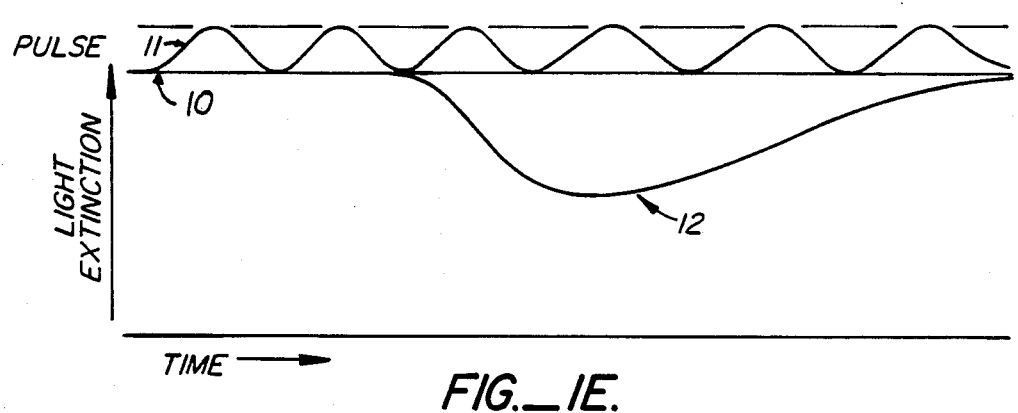
FIG._1E.
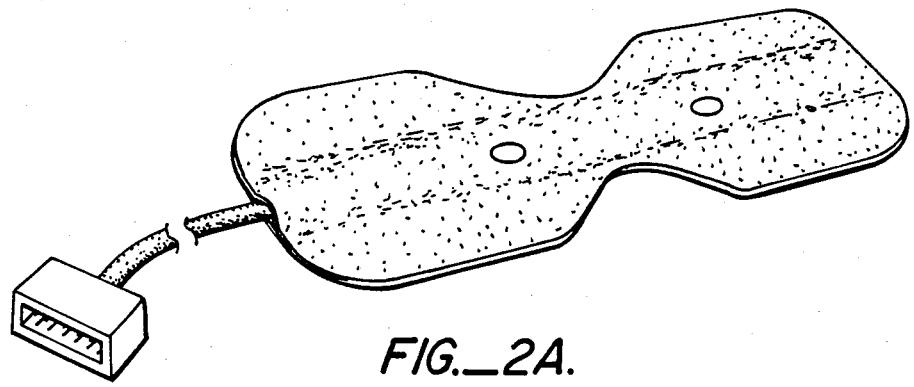
FIG._2A.

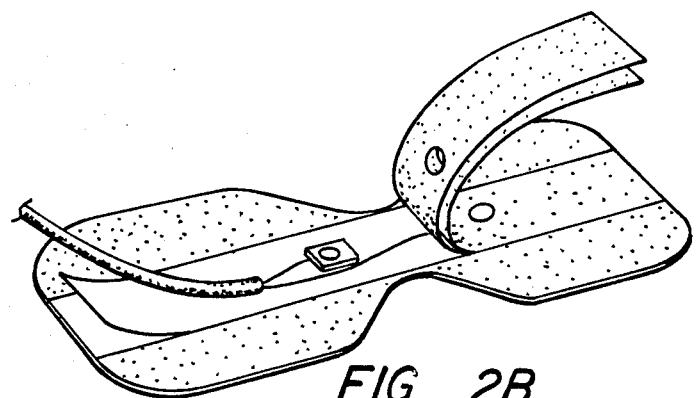
FIG._2B.
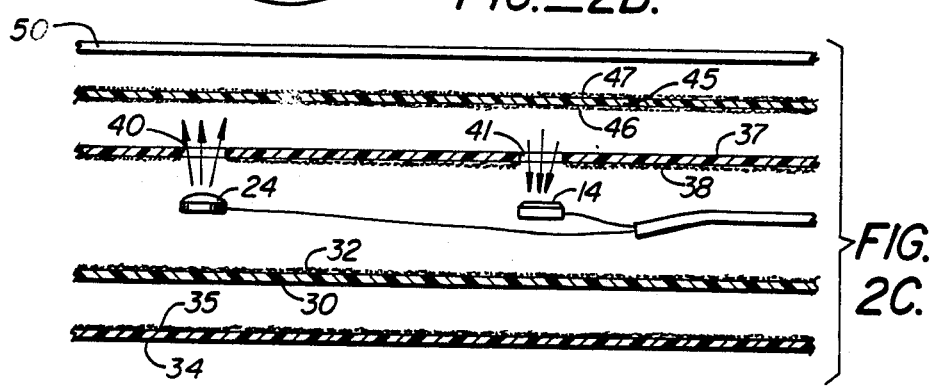
FIG. 2C.
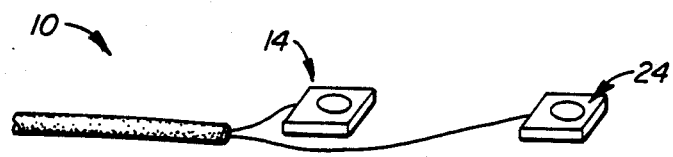
FIG._3A.
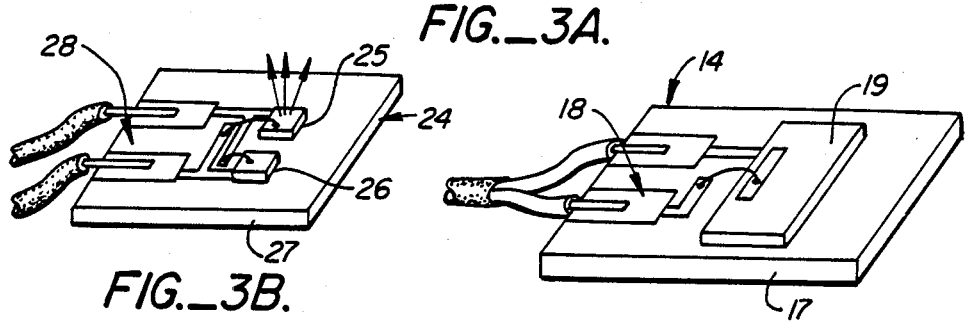
FIG._3B.
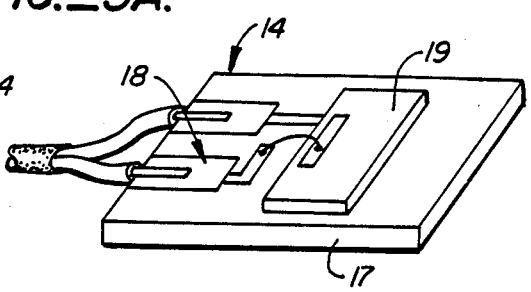
FIG._3C.
FIG._4.

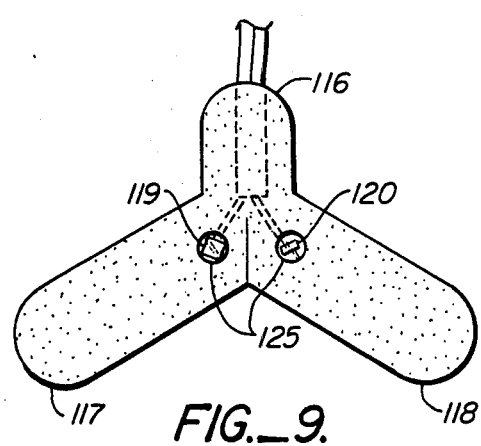
FIG._9.
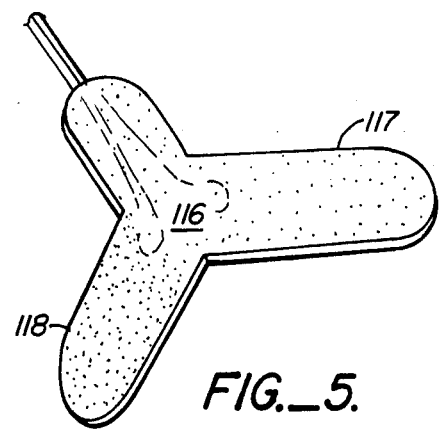
FIG._5.
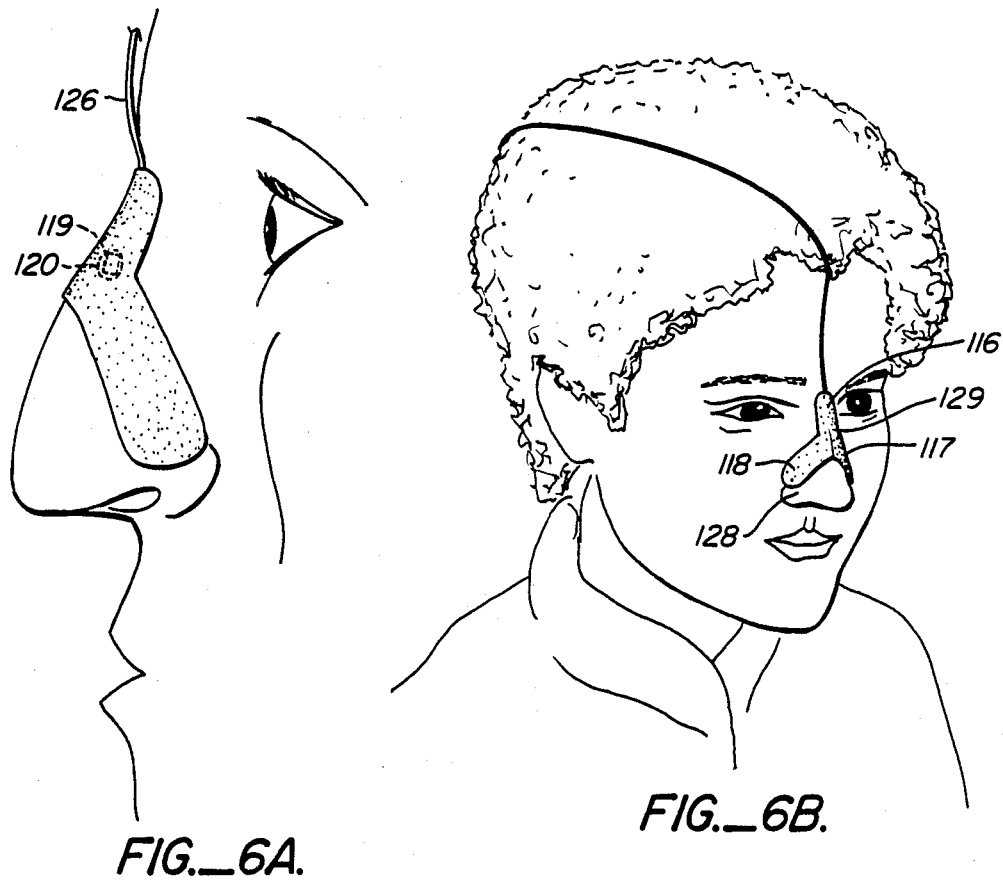
FIG._6A.
FIG._6B.

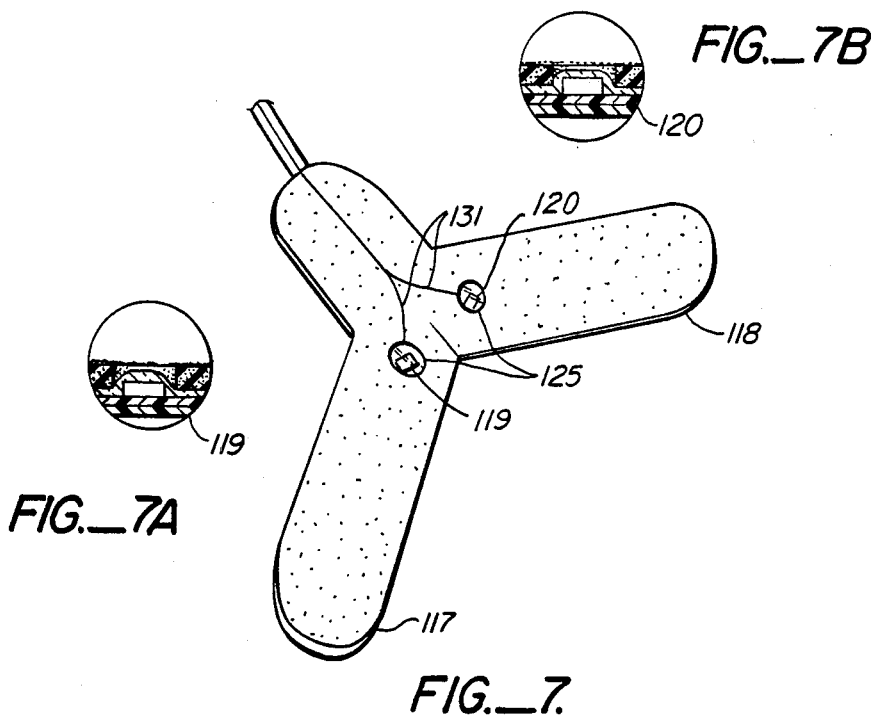
FIG._7B
FIG._7A
FIG._7.
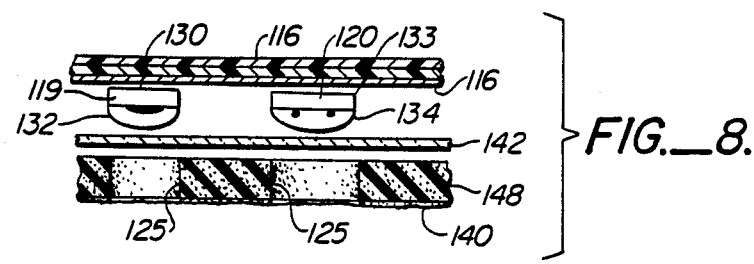
FIG._8.

SENSOR HAVING CUTANEOUS CONFORMANCE

This application is a continuation of copending United States patent application Ser. No. 873,129, filed June 11, 1986, abandoned which is a continuation of United States patent application Ser. No. 539,865, filed Oct. 7, 1983, now abandoned, which was a continuation-in-part of United States patent application Ser. No. 493,442, filed May 11, 1983, now abandoned.

This invention relates to a sensor having cutaneous conformance. More particularly, this sensor measures arterial oxygen saturation using non-invasive photoelectric determination, either on a digit or for rhinoplethysmography. A nasal optical sensor having physical conformance to the external cutaneous layer of the nasal septum is disclosed.

BACKGROUND OF THE INVENTION

Non-invasive monitoring of a patient's pulse is common in medical practice. One type of pulse monitor (plethysmograph) typically incorporates an incandescent lamp or light-emitting-diode (LED) to transilluminate, that is shine through, an area containing large amounts of blood. The light source is mounted to well-perfused flesh, such as a fingertip. Light is emitted and transilluminates the tissue. The amount of light passing through that tissue is measured using a photosensor. Changes between the light emitted by the light source and the light received by the photo-sensor are caused by changes in the optical absorption of the light by the blood perfusing the transilluminated tissue. Either broad-spectrum visual light or narrow bandwidth light in the red or infrared wavelengths can be used. The absorption of certain wavelengths is related to the oxygen saturation level of hemoglobin in the blood perfusing the transilluminated tissue. The variations in light absorption caused by change in oxygen saturations make possible direct measurement of the arterial oxygen content.

Instruments based on this principle have been designed that use two or more wavelengths to measure oxygen saturation and in some cases pulse rate.

A common problem with these types of oxygen sensors (oximeters) or pulse monitors (plethysmographs) is the incompatibility of their physical construction with the anatomy of the patient. A common plethysmograph monitor is a bulky rectangular sensor containing both a light-emitting-diode and a photo-sensor spaced approximately one quarter inch apart on the same side of the fleshy bottom portion of the fingertip (see FIG. 1A and 1B). This design suffers from a distortion of measurement commonly called motion artifact.

Motion artifact is due to differential motion between the sensor and the patient's finger as well as changes in pressure within the tissue. This type of design also suffers from poor signal pick-up during periods of low blood flow in the illuminated tissue. Low blood flow occurs when blood vessels constrict and/or when there is insufficient volume of circulating blood in the body. These conditions commonly occur during shock or periods of low body temperature. This particular type of construction has been used for measuring oxygen saturation with good technical results but the same problems with motion and loss of pulse. An additional problem with this design is that it is typically attached by a small hook and-loop strap type fastener of the type commonly sold under the trademark Velcro ®. This attachment design is easily dislodged from the finger either accidentally or involuntarily, terminating measurement prematurely and often unexpectedly.

Alternatively, a clamp design has been used to measure a patient's pulse. This design consists of one or more light-emitting-diodes adjacent to one side of a fleshy appendage such as a finger. The light from the LEDs is received by a photo-sensor placed on the opposing fleshy side of the appendage (see FIG. 1C and 1D). This type of construction generally consists of a small spring-loaded clip which attaches like a common clothespin to the tip of a finger or similar appendage. This type of sensor attachment has been used in an oximeter as well as a plethysmograph. The advantage of the clamp type of sensor attachment is that the optical path traverses through the nail and entire fingertip. This technique optically penetrates the tissue of the patient more deeply than does the simple single-sided surface sensor discussed previously.

This clamp type of sensor attachment suffers from some of the same defects as the single-sided type of sensor attachment in that it often yields inaccurate measurement due to distortion caused by motion artifact and also tends to be inadvertently removed. Further, the clamp type sensor attachment has one additional and serious drawback: The spring-loaded pressure on the fleshy tissue over a period of time will cause reduction of blood flow to the tissue. Reduction of blood flow causes loss of pulse amplitude and thus loss of the optical signal to be measured. To minimize this constrictive effect of the clamp type attachment, the sensor must be adjusted or repositioned frequently, generally once or twice per hour. This drawback makes this sensor's construction unacceptable for long term, uninterrupted measurement.

The phenomenon of motion artifact has been mentioned. Plethysmographs and oximeters operate on the principle that light extinction between the light source and the photo-sensor is the sum of two effects. The first effect is non-variant light extinction by stationary tissue. This would include skin, skin pigment, bone, nail, hair and other non-moving components of the tissue bed being illuminated. Referring to FIG. 1E, one identifies the non-variant component 10 of light extinction from stationary tissue shown with fixed amplitude over time.

The second effect of light pulsatile extinction is the time-variant absorption due to pulsatile arterial blood supplying the illuminated tissue bed. Referring to 11 on FIG. 1E, one sees that this is a quasi-sinusoidal pulse wave riding on top of the constant component 10 of light extinction. It is this second component that affords direct and accurate measurement of oxygen saturation in pulsatile arterial blood flow.

A sensor with appreciable mass or high aspect ratio is prone to developing relative motion between the light source, the photo-sensor and the tissue from minor mechanical disturbance. This relative motion creates concomitant variations in the light transmission from source to sensor and thus grossly distorts the measurement of light extinction. When this motion occurs, variances of light transmission are erroneous indicators of light extinction. These extinction errors ultimately cause corresponding errors in oxygen saturation measurement, all as a result of discontinuous contact and other causes of relative motion between the light source, the photo-sensor, and tissue. A possible profile of such a variant motion is shown in FIG. 1E as component 12.

In FIG. 1E, the sensor has moved transiently from the exact place where it had been fastened. The sensor moves due to a combination of high inertia caused by its substantial mass and poor conformance with the supporting tissue. Movement of the finger by the patient or some external disturbance causes relative motion between the sensor and finger. The change in light transmission created by this motion appears as a change in "light extinction" with time, designated as component 12 in FIG. 1E. The measuring instrument designed to monitor light extinction cannot distinguish optical data introduced to the sensor by the relative motion of the sensor from the optical data introduced by blood pulsation that the instrument is designed to analyze. Confusion of the instrument's logic inevitably results in inaccurate analysis of data from the oximeter and consequently erroneous measurement of oxygen saturation.

It should be evident that in situations where the sensor has significant mass relative to the finger and does not conform to the skin, motion artifact occurs with virtually every motion of the patient. When it is remembered that the patient may be unconscious and/or undergoing body motion, this motion, producing the artifactual component 12 in FIG. 1E, creates a serious impediment to consistent accurate measurement.

During severe physiologic stress, such as hypotension (low blood pressure), hypothermia (low body temperature), and shock (low blood flow), the bodily response is to constrict blood vessels (vasoconstriction) in order to divert blood away from the extremities and away from the periphery (the skin surface) to maximize blood flow to central vital organs (e.g., brain, heart, liver, etc.).

The internal carotid arteries are the major vessels carrying blood to the brain.

The nasal septum is the location of terminal branches of the internal carotid artery, namely, the anterior and posterior ethmoidal arteries. The nasal septum is recognized as an excellent place to monitor blood flow to the brain both because of the copious blood supply in this area (to warm incoming air) and because the branches of the carotid artery (including the anterior and posterior ethmoidal arteries) are among the last locations in the human body to suffer vasoconstriction under stress conditions.

Physicians have used surface mounted optical pulse sensors (plethysmographs) and optical oxygen saturation sensors (oximeters) fastened to body appendages (fingers, toes, ear lobes) with great success in healthy patients but with less success in critically ill and compromised patients. These surface sensors use two basic configurations. The first configuration (FIG. 1) comprises a small box-shaped sensor mounted onto a patient's digit by a hook and-loop fastener, (e.g., the product sold under the trademark Velcro ®). This design may suffer from unreliable measurement due to vasoconstriction and motion artifact. Motion artifact, which causes errant measurements, results from motion differential between the sensor and the flesh being interrogated; motion artifact can be induced by both voluntary and involuntary motion. Motion artifact causes relatively greater measurement errors when the desired pulse signal is very small during vasoconstriction.

Vasoconstriction is a narrowing of blood vessels resulting in a diminishing volume of blood flow to the tissue supplied by those vessels. Vasoconstriction commonly occurs when a patient suffers physiological shock resulting from trauma, accident, infection, or surgical complication. It also occurs when a patient, already in an intensive care unit, suffers further complications or worsening condition. Reduced pulse volume may also occur when an anesthesiologist deliberately induces very low blood pressure to minimize bleeding for a specific surgical operation. During vasoconstriction, there is less blood for the surface type sensor to measure. The result is a diminishing optical pulse signal and a relatively greater influence of motion artifact errors.

The second surface-type sensor configuration (FIG. 1D) that has been used to measure pulse and oxygen saturation consists of a spring-loaded clip shaped much like a clothes pin. This sensor is provided with a light source on one side of the clip and a photo detector on the other side to measure the degree of light extinction during transillumination by the blood flow in the tissue between the two sides of the clip. This second configuration is usually more effective than the first because the optical path, through the nail and the entire finger tip, penetrates much more deeply than the surface sensor (FIG. 1); however, vasoconstriction in critically ill patients coupled with the occluding spring pressure of the clip often results in insufficient pulse amplitude to reliably measure pulse or blood flow. Hence even a deep penetration surface sensor may not be useful in a critically ill or compromised patient.

SUMMARY OF THE INVENTION

A sensor for transillumination of a blood perfused portion of flesh to measure light extinction during transillumination is disclosed. The sensor is preferably mounted on a fingertip but any digit or other blood perfused tissue will work. The sensor conforms to and with the cutaneous layer of the blood perfused portion of flesh upon which the sensor is placed. The sensor is mounted on at least one flexible substrate.

The substrate includes a first end for disposition on one side of the flesh to be transilluminated and a second end for disposition on the opposite and opposed side of the flesh to be transilluminated, or there may be two independent substrates; one disposed on one side of the flesh to be transilluminated and the other one to be disposed on the opposite side of the flesh to be transilluminated.

A light source is mounted to the first end portion or first substrate and a photo-sensor is mounted to the second end portion or second substrate. The single flexible substrate may be elongated, and it may be provided with adhesive. The sensor is suitably windowed that light is allowed to take an optical path through the finger. If no flexible strip is used, the two ends are aligned and secured to the flesh such that the light emitted takes an optical path through the blood perfused flesh. If no adhesive is used, the substrates of the sensor may be fastened non-adhesively, such as with gauze, and non-invasively to the cutaneous layer of the flesh to be transilluminated.

When the sensor is adhesively fastened, the effect of the light source and photo-sensor being integrated into the adhesive fastener is that they become, in effect, a part of the skin. The resulting device is resistant to accidental removal and avoids constriction of blood vessels both internal and external. Most importantly, the low mass of the sensor itself and its conformance to the skin prevents motion, localized force, and the resulting contact interruption among the light source, photo-sensor and flesh. This feature eliminates the common interference associated with the operation of conventional plethysmographs and oximeters.

The present invention is directed to providing non-invasive, reliable, and continuous monitoring of the vital signs of a patient requiring intensive care to prevent vital organ damage or reduced biopotential. A nasal sensor is disclosed which measures light extinction during transillumination of the portion of nasal septum perfused by the ethmoidal arteries. The photoelectrical components, a light source and a light sensor, are embedded into a flexible adhesive substrate which is bifurcated into two arms. The substrate is also provided with signal connections leading to a measuring device. One arm of the bifurcated substrate is adhesed across the nasal septum. The entire apparatus is designed to orient the optical components to align the light source and sensor across the patient's nasal septum.

At least one light source is embedded in one arm. The light source conforms planarly to the substrate and is positioned to conform to the exterior cutaneous nasal layer while emitting light through the septum. At least one light sensor, embedded in the other arm, also conforms to the nose exterior and receives light which has transilluminated the septum.

Transilluminating the blood-perfused portion of the nasal septum yields information that includes, but is not limited to, oxygen saturation of the hemoglobin in the blood flow, the volume of individual blood pulsations supplied, and the rate and rhythm of blood pulsations.

An object of this invention is to disclose an apparatus for transilluminating well-perfused tissue with an interrogating light path between a light source and a photosensor. According to this aspect of the invention, the light source and photo-sensor are separately attached to remote end portions of electrical or other signal carrying connections sufficiently long for both portions to face one another from opposite sides of the tissue. The light source and photosensor mounted on a common flexible strip may then be adhesively fastened to the skin to transilluminate the desired portion of perfused tissue that both the source and the sensor now face. This disclosed adhesive fastening conforms the elements of the apparatus so completely to the patient's skin that motion artifact is eliminated. Hence, the light extinction measurement and resulting analysis to determine oxygen saturation and pulse rate is more accurate and less sensitive to interference.

A separate attachment for the light source and the photo-sensor, respectively, with or without direct adhesive could also be used and may be convenient for certain applications, such as a premature baby's hand. Indirect adhesive fastening, such as gauze wrapped around the hand and secured with adhesive tape, has also been used. Generally, however, the single strip facilitates alignment and is preferred.

A further advantage of this invention is that the plastic, flexible adhesive strip can be secured over the end of the fingertip, not circumferentially around the finger. This prevents restriction of blood flow to the tissue to be illuminated and measured. Only nominal pressure from this invention to the patient is applied locally to the patient on the topical skin layer directly holding the light source and the photosensor. This pressure does not extend across or into the perfused flesh in any way. There is no localized force exerted upon the flesh to be transilluminated. In sum, the flexible adhesive strip does not bind the perfused flesh. Consequently, the blood flow being interrogated is undisturbed.

A further advantage of the disclosed invention is the intimate adherence of the light source and the photosensor to the skin. This guards against accidental removal. A sensor is disclosed which effectively becomes a part of the patient and is not subject to natural rejections as might occur when a patient consciously or unconsciously registers and resists the tactile sense of a large, foreign mass attached to the skin.

A further object of this invention is to disclose a process for making the apparatus. In the assembly of this invention, the light source and the photosensor are mounted to substrates and are constructed of such small dimensions that both independently conform with a low aspect ratio to the flexible adhesive strip. This process also uses sequential layers of surgical tape, opaque vinyl, and light filters. Thereafter, apertured, opaque vinyl and finally a transparent adhesive layer are placed over the entire photo-sensor. The result is a simple flexible adhesive strip apparatus which is in conformance to the blood perfused flesh, i.e. digit, being interrogated for blood flow.

An advantage of this invention is that it is entirely disposable and thus sanitary. The resultant apparatus is non-invasive, is in full conformance to the skin and provides minimum interference with the motion and tactile sense of a patient.

An advantage of this invention is that the anterior ethmoidal artery (a branch of the major artery supplying blood to the brain) may be continuously monitored and measured for oxygen saturation, volume, pulse rate and rhythm. As the brain is one of the last organs to be denied blood in a critically ill or compromised patient, this apparatus satisfies a present need to provide information critical to patient treatment even under the most dire conditions.

A further advantage of this apparatus is that it is possible to monitor the critically ill and compromised patient who is already on a mechanical respirator to establish whether the artificially respirated oxygen is reaching the brain. Instantaneous and accurate diagnosis of arterial occlusion, among other symptoms, is now possible.

A further advantage is that the disclosed invention allows simultaneous monitoring of the critically ill patient for arterial oxygen saturation and for pulse rate rhythm and amplitude. With instantaneous, simultaneous and accurate measurements of a variety of vital signs, a physician may compare the disclosed invention's measurements to aid prognosis and identify trends.

Another advantage of this apparatus is that even under dire physiological conditions, the physiological housing, in which the sensor is seated, maintains consistent conditions which offers an unsurpassed monitoring site. A major function of the nose to the human body is to warm and humidify inspired air. The warming function of the nose ensures an adequate blood supply, even under severe physiological stress and peripheral vasoconstriction (described before) that commonly impedes the conventional surface-type plethysmograph and oximeters. Therefore, the nasal septum is an ideal location to make continuous and uninterrupted measurements of pulse and arterial saturation.

A further advantage of this invention is that the sensor is attached to the cutaneous layer of the nasal septum which neither invades nor interrupts the flow of the anterior and posterior ethmoidal arteries to be interrogated.

A further advantage of the disclosed invention is the critically ill patient's body need not be punctured and exposed to the risk of infection or some other further endangering of his condition.

A further advantage of the disclosed invention is the ability to measure oxygen saturation in the anterior and posterior ethmoidal arteries directly rather than indirectly. This ability to constantly measure blood oxygen content facilitates faster diagnosis of vital organ crises and makes feasible instantaneous and responsive treatment of the critically ill patient.

A further object of this invention is to disclose a method for manufacturing a nasal sensor. In the assembly of this invention, the light source and the photo-sensor are embedded in a flexible plastic substrate all of which are constructed of such small dimension that the sensor conforms cutaneously to the patient's external cutaneous layer. The assembly process entails sequential layers of mounting. There results a apparatus easily affixed on the patient's nose.

A further advantage of the disclosed external nasal sensor is that critical biopotential signals can be instantly and accurately received without competing for vital locations penetrating the nose. Interference with cannulaes, tubes, and sensing devices in the nose is avoided.

A further advantage of the disclosed nasal sensor is that the vital biopotential information may be accurately acquired from the critically compromised patient by technicians or persons who have little training or expertise.

A further advantage of the disclosed invention is that the blood flow of a critically compromised patient may be measured with limited risk of measurement error incurred by motion artifact; the foam layer between the adhesive and the substrate provides a tight, nonpressure exerting, skin seal which prevents motion artifact.

A further advantage of the disclosed invention is that the foam layer between the adhesive and the substrate provides a light-tight seal between the skin and the sensor, thus protecting the components and resulting measurement from the deleterious effects of ambient light.

A further advantage of the disclosed invention is that an opaque photographic coating applied to the foam/adhesive side of the flexible substrate prevents measurement inaccuracies by diminishing light refraction and rebound. The opaque photographic coating further protects against ambient light reaching the components.

A further advantage of the disclosed invention is that measurement of the carotid blood flow through the ethmoidal cavity is more accurate when the measurement site is located at the nasal external cutaneous layer rather than those measurements taken from sites at the inner nostril cutaneous layer.

A further advantage of the disclosed invention is that one size of sensing strip may be universally affixed to human noses. In contrast to the enormous variety of sizes, shapes, topical surface configurations of the human nostrils, the sizes and shapes of ridge environs of the human nose are relatively unvaried.

BRIEF DESCRIPTION OF DRAWINGS

Other objects, features and advantages of this invention will become more apparent after referring to the attached drawings in which:

FIGS. 1A and 1B are perspective illustrations of the prior art illustrating a common hook-and-loop type taping arrangement, using a light source and photo-sensor having appreciable mass which results in the defect herein described as motion artifact;

FIGS. 1C and 1D are diagrams of the clamping type sensor attachment across the digit of a patient;

FIG. 1E is a graphical representation of an instrument view of light extinction wherein motion artifact is present;

FIG. 2A is a perspective view of the sensor of this invention looking towards the photo-sensor, light-emitting-diodes and adhesive surface;

FIG. 2B is a view of the sensor of FIG. 2A illustrating various layers of this invention peeled back to expose the inner construction disclosed herein;

FIG. 2C is an exploded side view of the sensor wherein each of the composite elements of the preferred embodiment of the substrate are individually shown and identified;

FIG. 3A is a perspective view of the photosensor and light source used on the invention herein disclosed;

FIG. 3B is an enlargement view of a portion of FIG. 3A of a substrate having the light emitting diodes thereon;

FIG. 3C is an enlarged view of the remaining portion of FIG. 3A of a substrate for supporting the photo-sensitive surface;

FIG. 4 is a view of a digit with the cutaneous interrogating apparatus of this invention in place;

FIG. 5 is a perspective illustration of the nasal sensor;

FIGS. 6A and 6B are side and perspective views of patients with the disclosed invention in place anatomically;

FIG. 7 is a perspective view of the nasal sensor showing the assembly mount of the light-emitting-diode and of the photo-sensor with sectional enlarged views of the light-emitting-diode and the photo-sensor;

FIG. 8 is an exploded illustration of flexible substrate, foam, electrical component and other layers designed to monitor blood flow across the nasal septum; and FIG. 9 is a bottom plan view of a nasal sensor according to the invention.

DETAILED DESCRIPTION OF THE PREFERRED EMBODIMENT

In the description that follows, we will first describe the construction of the sensor device 10 herein. Thereafter, we will set forth the attachment to the perfused flesh being examined.

Referring to FIG. 3A, two substrate portions 14, 24 are illustrated. To portion 14 is mounted a photo-sensor. To portion 24 are mounted the light sources of this invention. The light sources will be discussed first with respect to FIG. 3B.

Light-emitting-diodes 25 and 26 are adhesively fastened to a substrate 27 as by gluing with electrically conductive epoxy adhesive. Very small dimensional light-emitting-diodes with micro circuitry can be utilized. These light-emitting-diodes will be seen by the reader to conform to a thin layer which is subsequently fastened in the plane of substrate 27.

By way of dimensions, substrate 27 is typically 4 mm×6 mm or such other dimensions may be used. Electrical connections 28 are used and include paired light-emitting-diode driving conductors with a common ground.

Referring to FIG. 3C, the photo-sensitive portion of device 10 can be seen. This photo-sensitive portion includes a substrate 17, electrical connections 18 and a photo-sensitive surface 19 adhesively fastened to plate 17. Again the dimensions are provided which give the apparatus low profile and aspect ratios.

It should be apparent that the electrical connections herein disclosed can be subject to other configurations. For instance, an integrated chip or thin film construction may be desirable where mass production of the element herein disclosed occurs.

In the preferred embodiment as of the date of this disclosure, the elements are covered on the photoactive side with a transparent epoxy layer. We prefer that a clear layer of epoxy be placed over the construction of 3B for insulation and light transmission and that a red layer be placed over the substrate 17 of FIG. 3C to shield the photo-sensor from ambient spectra outside of the desired red and infrared angstrom wavelengths.

The sequential construction of the preferred embodiment of this invention can best be illustrated with respect to FIG. 2C. Referring to FIG. 2C, it can be seen that the photo-active elements of the sensor substrate 14, 24 are fastened with the inactive side down to an opaque vinyl strip 30 having an adhesive surface 32. Likewise, a porous, flexible adhesive tape overlies the opaque vinyl strip 30 and a porous flexible tape layer 34 having an adhesive side 35. Referring to the figure of FIG. 2B, one can see that tape 35 is elongate and formed in a butterfly design. That is to say that the distal ends of the shape are relatively wide and the medial end connecting portion is narrow, the construction being suitably rounded. This configuration has been found especially preferably for attachment to a finger.

Once the photo-active elements 14, 24 are attached, a second opaque vinyl tape is placed over the photo-active elements at 37. This tape has a downwardly exposed adhesive layer 38 and effects capture of the light source substrate and the photo-sensor substrate between strip 30 and strip 37.

Strip 37 is apertured at respective apertures 40,41. These apertures allow light to pass. At the same time, they conform the thickness of the photo-active substrates to the overall thickness of the flexible adhesive strip to which attachment occurs. The photoactive substrates as thus captured are ideally indistinguishable in the tactile sense from the flexible adhesive strip itself.

Finally, a layer of clear polyester 45 having double adhesive coatings 46, 47 is placed over the central narrow length of the flexible adhesive strip. This enables the passage of light and yet ensures intimate bonding of the photo-sensor to the skin and the flexible adhesive strip.

A protective layer of release tape 50 protects the entire article during manufacture and before use.

It will be understood that the flexible adhesive strip layer 34 and the release tape layer 50 are both given the elongate butterfly configuration. The remaining tape elements herein disclosed have an overall narrow rectangular shape extending the entire length of the flexible adhesive strip.

Referring to FIG. 4, the invention herein is shown fastened over a fingertip. Simply stated, the distal ends fasten over and encompass the blood perfused digit.

Light is emitted and transilluminates the blood-perfused digit.

It should be noted that while this is the preferred configuration for use with fingertips, other shapes may be suitable for other appendages, such as toes, or a hand or foot.

Additionally, a variation in construction would optimize the sensor for use with premature babies where the use of tape is injurious to skin. By eliminating the adhesive layers facing the tissue a sensor is made that may be bandaged in place using methods suitable for such tiny children.

The present disclosure also finds preferred location on the skin of the nasal septum overlying the carotid cavity.

Turning to the figures, in FIGS. 9, 5, 6A and 6B, the invention includes a substrate 116, bifurcated substrate arms 117, 118, a set of photo-electric components 119, 120, and other layers.

The preferred embodiment will be described with the photo-electric components 119, 120 mounted to and aligned on opposing nasal arms 117, 118.

Referring now to FIGS. 7 and 8, the substrate 116 is made of flexible plastic composition having some elasticity. The side to be affixed to the foam is coated with an opaque photographic layer 142. A spongy thin foam layer 148 is applied upon the opaque photographic coating 142. To the spongy thin foam layer 148, medical grade adhesive 140 is affixed. The substrate 116 includes apertures 125 for permitting the transmission of light.

When the disclosed invention is located on a human nose, FIGS. 6A and 6B, the substrate 116 conforms closely to the outer nose ridge 126, with each of the two nasal arms 117, 118 firmly seated on the exterior sides of the nose 128, 129. The arms 117, 118 are adhesively held in position.

The adhesive 140 provides the arms with stationary conformance to the septum without occluding the blood flow to be interrogated. So close is the resulting conformance of the arms 117, 118 to the external cutaneous layer of the nose that the sensor effectively becomes a part of that cutaneous portion. Competition for tubular access to the nasal breathing apertures of the patient is not present due to the completely exterior placement of the nasal sensor.

Referring to FIGS. 7 and 8, the photo-sensor 119 includes a ceramic substrate 130, electrical connections 131 and a transparent sealant 132 fastened to the ceramic substrate 130 by gluing and by microcircuitry 131. The light-emitting-diode 120 includes a ceramic substrate 133, electrical connections 131 and a transparent sealant 134 fastened to the ceramic substrate 133 by gluing and by microcircuitry 131. By way of dimension, each of the ceramic substrates 133 is 4 mm×6 mm or of such other diminutive proportions as may be useful.

The light-emitting-diode 120 and the photoelectric sensor 119 are mounted into substrate arms 117, 118 being provided with respective apertures 125. FIG. 6A represents a side and isometrical view of the light-emitting-diode 120 and the photo-electric sensor 119. It will be observed that this invention has planar conformity to the nasal surface despite the variations in nasal configurations from one person to the next.

Using the sensor proceeds as follows: user affixes one of the two substrate arms 117, 118 onto one side of the human nose, the second substrate arm going onto the other side of the human nose (FIGS. 6A and 6B.) The base of the flexible substrate 116 seats firmly against the nose ridge 129.

The substrate arms 117, 118 conform closely to the cutaneous layer of the nose. The close conformity allows, but does not occlude, the septal blood flow to be interrogated.

Once the base and arms are in place, the light-emitting-diode 120 transmits light into the vicinity of the septum. The photo-electric-sensor receives light after such light has transilluminated the septum.

Other modifications and variations may be made to the present embodiment without departing from what is regarded as the invention.

What is claimed is:

1. A non-invasive, electrooptical sensor probe for removable adhesive attachment to a convex portion of the skin of a patient for use in measuring light extinction during transillumination of the blood-perfused tissue beneath said skin comprising:
    a flexible, initially substantially planar, web-like support structure having substantially parallel, spaced, oppositely facing upper and lower surfaces;
    a light source mounted in the web of said support structure, said light source having a light-emitting surface facing in the same direction as said lower surface;
    a photo-sensor mounted in the web of said support structure, said photo-sensor having a light-responsive surface facing in the same direction as said lower surface, said photo-sensor being spaced from said light source in the plane of said support structure; and
    an adhesive layer on said lower surface for removably adhesively securing said lower surface to said convex portion of said skin so that said lower surface is held in conformance with said skin, said support structure being flexible also to conform to said skin without stressing either of said skin and the underlying tissue at any time during operation of said sensor probe, the convexity of said skin portion between the locations of said light source and said photo-sensor causing said light-emitting and light-responsive surfaces to be inclined toward one another so that light from said light source transilluminates the tissue between said light source and said photo-sensor and said light-responsive surface receives at least a part of said light.

2. The apparatus defined in claim 1 wherein said support structure comprises:
    a lower layer which is relatively opaque except at the locations of said light source and photo-sensor, where said lower layer is relatively transparent;
    an upper layer; and
    means for adhesively securing said upper and lower layers together with said light source and photo-sensor captured therebetween.

* * * * *